United States Patent
Parvulescu et al.

(10) Patent No.: US 10,766,840 B2
(45) Date of Patent: Sep. 8, 2020

(54) PROCESS FOR PREPARING AN UNSATURATED ALCOHOL

(71) Applicant: BASF SE, Ludwigshafen am Rhein (DE)

(72) Inventors: Andrei-Nicolae Parvulescu, Ludwigshafen am Rhein (DE); Miriam Bru Roig, Ludwigshafen am Rhein (DE); Albert Werner, Bishop, TX (US); Bernhard Brunner, Ludwigshafen am Rhein (DE); Wolfgang Siegel, Ludwigshafen am Rhein (DE); Stephan Maurer, Ludwigshafen am Rhein (DE); Ulrich Mueller, Ludwigshafen am Rhein (DE); Michael Ludwig Lejkowski, Heidelberg (DE)

(73) Assignee: BASF SE (DE)

( * ) Notice: Subject to any disclaimer, the term of this patent is extended or adjusted under 35 U.S.C. 154(b) by 0 days.

(21) Appl. No.: 16/488,962

(22) PCT Filed: Feb. 27, 2018

(86) PCT No.: PCT/EP2018/054799
§ 371 (c)(1),
(2) Date: Aug. 27, 2019

(87) PCT Pub. No.: WO2018/158244
PCT Pub. Date: Sep. 7, 2018

(65) Prior Publication Data
US 2020/0002255 A1    Jan. 2, 2020

(30) Foreign Application Priority Data
Feb. 28, 2017 (EP) .................................... 17158348

(51) Int. Cl.
C07C 29/38 (2006.01)
B01J 29/40 (2006.01)
B01J 29/46 (2006.01)
B01J 29/70 (2006.01)

(52) U.S. Cl.
CPC .............. *C07C 29/38* (2013.01); *B01J 29/405* (2013.01); *B01J 29/46* (2013.01); *B01J 29/7057* (2013.01); *B01J 29/7088* (2013.01)

(58) Field of Classification Search
CPC ......... C07C 29/38; B01J 29/405; B01J 29/46; B01J 29/7057; B01J 29/7088

USPC .......................................................... 568/879
See application file for complete search history.

(56) References Cited

U.S. PATENT DOCUMENTS

| | | | |
|---|---|---|---|
| 10,202,323 B2 | 2/2019 | Parvulescu et al. |
| 10,308,508 B2 | 6/2019 | Saloway |
| 2011/0054083 A1 | 3/2011 | Lorenz et al. |
| 2012/0059177 A1 | 3/2012 | Gralla et al. |
| 2018/0362351 A1 | 12/2018 | Parvulescu et al. |
| 2018/0362353 A1 | 12/2018 | Vautravers et al. |
| 2019/0077779 A1 | 3/2019 | Riedel et al. |

FOREIGN PATENT DOCUMENTS

| | | | |
|---|---|---|---|
| WO | WO-2011147919 A1 | 12/2011 |
| WO | WO-2011154330 A1 | 12/2011 |
| WO | WO-2014060259 A1 | 4/2014 |
| WO | WO-2014060261 A1 | 4/2014 |
| WO | WO-2015067654 A1 | 5/2015 |

OTHER PUBLICATIONS

Zhao Yang et al, Journal of Industrial and Engineering Chemistry, vol. 20, No. 6, Nov. 1, 2014, pp. 4146-4151.*
Fei Y., et al., "Enhanced activity of MCM-48 based tin catalyst for synthesis of 3-methylbut-3-en-1-ol by adjusting the mesochannel environment", Journal of Industrial and Engineering Chemistry, vol. 20, No. 6, (2014), pp. 4146-4151.
Fernandes, R., et al., "PCC-mediated novel oxidation reactions of homobenzylic and homoallylic alcohols" Tetrahedron Letters vol. 44, No. 6, (2003), pp. 1275-1278.
International Preliminary Report on Patentability for PCT/EP2018/054799 dated May 3, 2018.
Yashima, T., et al., "Synthesis of 3-methyl-3-butene-1-ol from isobutene and formaldehyde on FeMCM-22 zeolites", part of "Porous Materials in Environmentally Friendly Processes", eds. I, Kiricsi, et al., Studies in Surface Science and Catalysis, vol. 125, (1999), pp. 507-514.

* cited by examiner

*Primary Examiner* — Deborah D Carr
(74) *Attorney, Agent, or Firm* — Faegre Drinker Biddle & Reath LLP

(57) ABSTRACT

The present invention relates to a process for preparing an unsaturated alcohol, preferably 3,7-dimethyl-2,6-octadienal, by contacting an alkene, preferably isobutene, with formaldehyde in the presence a condensation catalyst comprising a zeolitic material comprising the framework structure of which comprises a tetravalent element Y other than Si.

17 Claims, No Drawings

PROCESS FOR PREPARING AN UNSATURATED ALCOHOL

CROSS-REFERENCE TO RELATED APPLICATIONS

This application is a national stage application (under 35 U.S.C. § 371) of PCT/EP2018/054799, filed Feb. 27, 2018, which claims benefit of European Application No. 17158348.7.

The present invention relates to a process for preparing a compound of formula (II),

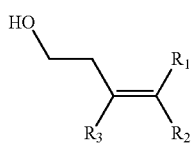
(II)

preferably 3-methyl-3-buten-1-ol (isoprenol), by contacting a compound of formula (I),

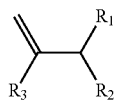
(I)

preferably 2-methylpropene (isobutene), with formaldehyde with a condensation catalyst which comprises an aluminum-free zeolitic material and, in addition to Si, a tetravalent element Y other than Si.

Isoprenol is an important monomeric starting material for preparing 3,7-dimethyl-2,6-octadienal (citral) and/or the E-isomer of 3,7-dimethyl-2,6-octadienal (geranial) and/or the Z-isomer of 3,7-dimethyl-2,6-octadienal (neral). Citral, geranial and neral are commonly used as aroma chemical compounds.

Komatsu et al. (Porous Material in Environmentally Friendly Processes, vol. 125, 1999) discloses a zeolite having framework structure type MCM which is used in the Prins reaction of aqueous formaldehyde and isobutene for preparing isoprenol. The molar ratio of isobutene relative to formaldehyde used in this reaction is a quite high ratio of 21:1.

Further, the conversion of isobutene to isobutenol via Prins reaction usually requires high pressures and high temperatures. The process becomes economically attractive only when it is carried out under mild conditions and with high conversion and selectivity.

Zhaoyang et al. discloses tin incorporated MCM-48 catalysts for condense-esterification of paraformaldehyde, isobutene and acetic acid to produce MB-AC (3-methylbut-3-en-1-ol) and MBOH (3-methylbut-3-en-1-ol).

Fernandes et al. discloses a PCC-mediated carbon-carbon bond cleavage reaction during oxidation of homobenzylic alcohols leading to the formation of benzylic carbonyl compounds.

There was still a need to develop an improved catalytic process for preparing an unsaturated alcohol starting from formaldehyde and an alkene, such as isobutene which is carried out in mild conditions, with a lower excess of reagent and yet lead to the desired product in a high conversion with high selectivity. One of the problems addressed by the present invention was therefore to provide an improved catalytic process for preparing a compound of formula (II) such as isoprenol starting from formaldehyde and an alkene.

It has been surprisingly found that such an improved process can be provided by using a condensation comprising a specific zeolitic material as catalytically active component. More particularly, it has been found that the improved process is advantageous in terms of at least one, in particular all of the parameters of yield, selectivity, and conversion. The process of the present invention further advantageously allows using a low molar ratio of isobutene relative to formaldehyde. Further the reaction according to the present invention can be carried out at mild conditions of temperature and pressure. Further, it was found that the process of the invention can be carried out using aqueous formaldehyde as aldehyde source which, in contrast to paraformaldehyde or other formaldehyde sources, has by far the highest relevance for an industrial-scale process.

The present invention therefore relates to a process for preparing compound of formula (II)

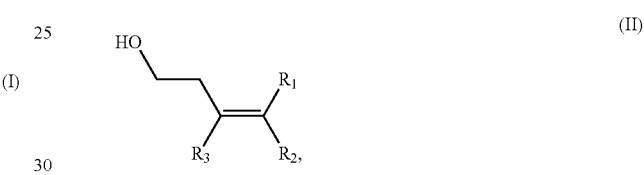
(II)

the process comprising
(i) providing a mixture comprising formaldehyde and a compound of formula (I)

(I)

(ii) contacting the mixture provided in (i) with a condensation catalyst comprising a zeolitic material, obtaining a mixture (ii) comprising the compound of formula (II);
wherein $R_1$, $R_2$ and $R_3$ are independently of each other selected from the group consisting of H, optionally substituted $C_1$-$C_{10}$ alkyl, optionally substituted $C_2$-$C_{10}$ alkenyl, and optionally substituted aryl having from 6 to 12 carbon atoms;
wherein the framework structure of the zeolitic material in (ii) comprises Si, O, optionally Al, and a tetravalent element Y which is one or more of Sn, Ti and Zr, and wherein in the framework structure of the zeolitic material in (ii), the molar ratio Al:Si, calculated as elemental aluminum and silicon, is in the range of from 0:1 to 0.001:1.

The term "$C_1$-$C_{10}$ alkyl" as used in the context of the present invention refers to a linear or branched and optionally suitably substituted alkyl residue having, in its carbon atom chain, 1, 2, 3, 4, 5, 6, 7, 8, 9, or 10 carbon atoms, and includes, but is not limited to, methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, and n-octyl.

The term "$C_2$-$C_{10}$ alkenyl" as used in the context of the present invention refers to a linear or branched and optionally suitably substituted alkenyl residue having, in its carbon atom chain, 2, 3, 4, 5, 6, 7, 8, 9, or 10 carbon atom and includes, but is not limited to, ethenyl, 2-propenyl, 2-butenyl, 3-butenyl, 2-pentenyl and its chain isomers, 2-hexenyl and 2,4-pentadienyl.

The term "aryl having from 6 to 12 carbon atoms" as used in the context of the present invention is understood to include, but is not limited to phenyl, naphthyl, indanyl, or 1,2,3,4-tetrahydronaphthyl.

The term "optionally substituted" as used in the context of the present invention is to be understood to include, but not limited to any suitable substituent conceivable for the skilled person to be comprised in the compound of formula (I) which does not prevent the formation of the compound of formula (II) according to the present process. Suitable substituents are, for example, F, Cl, I, Br, $C_1$-$C_{10}$ alkyl, $C_2$-$C_{10}$ alkenyl, and aryl having from 6 to 12 carbon atoms.

Preferably, $R_1$ and $R_2$ are each H and $R_3$ is $C_1$-$C_{10}$ alkyl. More preferably, $R_1$ and $R_2$ are each H and $R_3$ is $CH_3$. Therefore, the compounds of formulas (I) and (II) are preferably the compounds of formulas (I') and (II'):

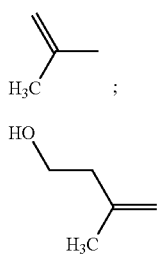
(I')

(II')

Therefore, the present invention preferably relates to a process for preparing compound of formula (II')

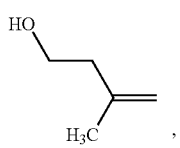
(II')

the process comprising (i) providing a mixture comprising formaldehyde and a compound of formula (I')

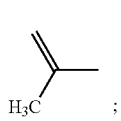
(I')

(ii) contacting the mixture provided in (i) with a condensation catalyst comprising a zeolitic material, obtaining a mixture comprising the compound of formula (II');

wherein the framework structure of the zeolitic material in (ii) comprises Si, O, optionally Al, and a tetravalent element Y which is one or more of Sn, Ti and Zr, and wherein in the framework structure of the zeolitic material in (ii), the molar ratio Al:Si, calculated as elemental aluminum and silicon, is in the range of from 0:1 to 0.001:1.

The term "condensation" as used in the context of the present invention is to be understood as an olefin-aldehyde condensation reaction in which an unsaturated alcohol, the compound of formula (II) in the present case, is formed by the addition of formaldehyde to an alkene of formula (I). A preferred condensation reaction is the Prins condensation reaction, a catalysed condensation reaction of an aldehyde to an alkene resulting in an unsaturated alcohol.

Preferably, at least step (ii) of the process according to the present invention is carried out in continuous mode. If step (i) is carried out in continuous mode and step (ii) is carried out in continuous mode, the process comprising steps (i) and (ii) is a continuous process. If step (i) is carried out in batch mode and step (ii) is carried out in continuous mode, the process comprising steps (i) and (ii) is a semi-continuous process.

In step (i) of the process according to the invention, a mixture comprising formaldehyde and a compound of formula (I) is provided.

Preferably, formaldehyde is provided as one or more of aqueous formaldehyde, trioxane, and paraformaldehyde. Trioxane is a heterocyclic compound of the group of the acetals which is formed by trimerization of formaldehyde. Paraformaldehyde is the short-chain polymer of formaldehyde, typically having a degree of polymerization of from 8 to 100. More preferably, the formaldehyde is provided as aqueous formaldehyde. More preferably, the aqueous formaldehyde comprises the formaldehyde, calculated as $CH_2O$, in an amount in the range of from 30 to 80 weight-%, more preferably in the range of from 45 to 75 weight-%, more preferably in the range of from 60 to 70 weight-%, based on the total weight of the aqueous formaldehyde.

Compounds of formula (I), such as isobutene, are generally commercially available.

The mixture of (i) may in principle have any molar ratio of the compound of formula (I) relative to formaldehyde, calculated as $CH_2O$, suitable for obtaining the compound of formula (II). Preferably, the molar ratio of the compound of formula (I) relative to formaldehyde calculated as $CH_2O$, in the mixture provided in (i) is in the range from 1:1 to 12:1, preferably in the range of from 5:1 to 11.5:1, more preferably in the range of from 9:1 to 10:1. More preferably, the molar ratio of the compound of formula (I) to formaldehyde, calculated as $CH_2O$, in the mixture provided in (i) is in the range from 1:1 to 9:1, more preferably in the range of from 1:1 to 7:1, more preferably in the range from 1:1 to 6:1, more preferably in the range of from 1.5:1 to 5.1:1, more preferably in the range of from 1.7:1 to 5:1, more preferably in the range of from 2:1 to 5:1, more preferably in the range of from 2.5:1 to 5:1.

It is preferred that the mixture provided in (i) and contacted with the condensation catalyst in (ii) contains acetic acid in an amount in the range of from 0 to 500 weight-ppm, preferably in the range of from 0 to 250 weight-ppm, more preferably in the range of from 0 to 100 weight-ppm. More preferably, the mixture provided in (i) and contacted with the condensation catalyst in (ii) does not comprise acetic acid.

Therefore, the present invention preferably relates to a process for preparing a compound of formula (II')

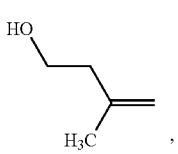   (II')

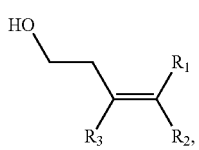   (II)

the process comprising
(i) providing a mixture comprising aqueous formaldehyde and a compound of formula (I')

the process comprising
(i) providing a mixture comprising aqueous formaldehyde, a solvent and a compound of formula (I)

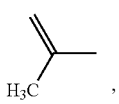   (I')

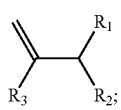   (I)

wherein the molar ratio of the compound of formula (I) relative to formaldehyde calculated as $CH_2O$ is in the range from 1:1 to 12:1;
(ii) contacting the mixture provided in (i) with a condensation catalyst comprising a zeolitic material, obtaining a mixture comprising the compound of formula (II');
wherein the framework structure of the zeolitic material in (ii) comprises Si, O, optionally Al, and a tetravalent element Y which is one or more of Sn, Ti and Zr, and wherein in the framework structure of the zeolitic material in (ii), the molar ratio Al:Si, calculated as elemental aluminum and silicon, is in the range of from 0:1 to 0.001:1.

In principle, the mixture of (i) can be provided at any temperature suitable for the process according to the invention. The mixture provided in (i) can therefore be provided, for example, at a temperature corresponding to room temperature, or else be heated prior to contacting with the condensation catalyst comprising the zeolitic material to obtain a mixture comprising the compound of formula (II). It is equally conceivable that the mixture of (i) is cooled to a temperature suitable for the process according to the invention, if individual components or all the components of the mixture of (i) would otherwise have an undesirably high temperature for the process according to the invention. Preferably, the mixture provided (i) is brought to a temperature in the range of from 50 to 150° C. before being contacted with the condensation catalyst comprising a zeolitic material according to (ii). More preferably, the mixture provided in (i) is brought to a temperature in the range of from 80 to 120° C., more preferably in the range of from 95 to 110° C. before being contacted with the condensation catalyst comprising a zeolitic material according to (ii).

In addition to the compound of formula (I) and the formaldehyde, the mixture provided in (i) may comprise further components. For example, the mixture provided in (i) may comprise one or more solvents. It is possible to use all suitable solvents which are known to those skilled in the art. Preferably, the solvent is one or more of 3-methyl-2-buten-1-ol (prenol), ethylhexanol, methanol, acetonitrile, ethyl acetate, tert-butanol, water and acetone. More preferably, the solvent is one or more of water, tert-butanol and ethyl acetate. More preferably, the solvent is tert-butanol or a mixture of tert-butanol and water.

Therefore, the present invention preferably relates to a process for preparing compound of formula of formula (II)

wherein the molar ratio of the compound of formula (I) relative to formaldehyde, calculated as $CH_2O$, is in the range from 1:1 to 12:1 and wherein the solvent is one or more of 3-methyl-2-buten-1-ol (prenol), ethylhexanol, methanol, acetonitrile, ethyl acetate, tert-butanol, water and acetone. More preferably, the solvent is one or more of water, tert-butanol and ethyl acetate, preferably, the solvent is tert-butanol or a mixture of tert-butanol and water
(ii) contacting the mixture provided in (i) with a condensation catalyst comprising a zeolitic material, obtaining a mixture comprising the compound of formula (II);
wherein the framework structure of the zeolitic material in (ii) comprises Si, O, optionally Al, and a tetravalent element Y which is one or more of Sn, Ti and Zr, and wherein in the framework structure of the zeolitic material in (ii), the molar ratio Al:Si, calculated as elemental aluminum and silicon, is in the range of from 0:1 to 0.001:1.

Therefore, the present invention preferably relates to a process for preparing compound of formula (II')

   (II')

the process comprising
(i) providing a mixture comprising aqueous formaldehyde, a solvent and a compound of formula (I')

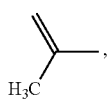   (I')

wherein the molar ratio of the compound of formula (I') relative to formaldehyde, calculated as $CH_2O$, is in the range from 1:1 to 12:1 and wherein the solvent is tert-butanol or a mixture of tert-butanol and water;
(ii) contacting the mixture provided in (i) with a condensation catalyst comprising a zeolitic material, obtaining a mixture comprising the compound of formula (II');

wherein the framework structure of the zeolitic material in (ii) comprises Si, O, optionally Al, and a tetravalent element Y which is one or more of Sn, Ti and Zr, and wherein in the framework structure of the zeolitic material in (ii), the molar ratio Al:Si, calculated as elemental aluminum and silicon, is in the range of from 0:1 to 0.001:1.

The solvent can be supplied to the process, for example, as fresh solvent. It is equally possible to recycle the solvent within the process by means of one or more recycling steps. It is equally possible to supply a portion of the solvent to the process as fresh solvent and to recycle a further portion of the solvent within the process by means of one or more recycling steps.

Preferably, the amount of formaldehyde in the mixture provided in (i), calculated as CH2O, relative to the solvent is in the range of from 1 to 50 weight-%, more preferably in the range of from 1 to 20 weight %.

Preferably, the mixture provided in (i) is provided as a liquid mixture.

The framework structure of the zeolitic material according to (ii) comprises Si, O and H. In addition, the framework structure of the zeolitic material according to (ii) has a molar Al:Si ratio, calculated as elemental Al and Si, in the range of from 0:1 to 0.001:1. Preferably, the framework structure of the zeolitic material in (ii) has a molar Al:Si ratio in the range of from 0:1 to 0.0001:1, more preferably in the range of from 0:1 to 0.00001:1, more preferably in the range of from 0:1 to 0.000001:1. Preferably, the framework structure of the zeolitic material in (ii) is free of aluminum. The term "free of aluminum" as used in this context of the present invention means that aluminium is present in the zeolitic material, if at all, only in traces, i.e. in the form of unavoidable impurity.

The framework structure of the zeolitic material according to (ii), in addition to Si, O, H and optionally Al, comprises a tetravalent element Y which is one or more of Sn, Ti and Zr. It is preferred that at least 99 weight-%, more preferably at least 99.5 weight-%, more preferably at least 99.9 weight-% of the framework structure of the zeolitic material according to (ii) consist of Si, Y, O and H, For example, at least 99.95 weight-% or at least 99.99 weight-% of the framework structure of the zeolitic material according to (ii) consist of Si, Y, O and H.

Preferably, the amount of the tetravalent element Y in the framework structure of the zeolitic material according to (ii) is in the range of from 0.5 to 20 weight-%, more preferably in the range of from 1 to 18 weight-%, more preferably in the range of from 1.5 to 17 weight-%, more preferably in the range of from 4 to 16 weight-%, based on the total weight of the zeolitic material.

It is further preferable that the framework structure does not comprise a trivalent element X which is B, more preferably does not comprise a trivalent element X which is one or more of B, In, Ga, and Fe, more preferably does not comprise a trivalent element X, other than optionally Al. In the context of the present invention, the term "no element X other than optionally Al" is to be understood in that the amount of the trivalent element X is in the range of from 0 to 1 weight-%, preferably in the range of from 0 to 0.1 weight-%, more preferably in the range of from 0 to 0.01 weight-%. The term "no element X" as used in this context of the present invention means that the element X is present in the zeolitic material, if at all, only in traces, i.e. in the form of unavoidable.

Zeolitic materials, in the context of the present application, are naturally occurring or synthetically produced microporous crystalline materials having a three-dimensional framework structure formed from corner-linked tetrahedra. Preferably, the zeolitic material according to (ii) has acid sites comprising Brønsted and/or Lewis acid sites. Accordingly, the zeolitic material according to (ii) preferably has one desorption maximum in its desorption spectrum obtained by temperature-programmed desorption with $NH_3$ ($NH_3$-TPD) as described in Reference Example 1.4 herein. Preferably, the zeolitic material according to (ii) has a desorption maximum within the temperature ranges of from 0 to 250° C., in a temperature-programmed desorption with $NH_3$. The zeolitic material of the invention more preferably do not have ammonia desorption above 250° C., in a temperature-programmed desorption with $NH_3$. Without being bound to any theory it has been seen that the selectivity of the reaction is improved by using a catalyst comprising a zeolitic material that exhibits a desorption maximum within the temperature ranges of from 0 to 250° C.

The present invention therefore relates to a process for preparing compound of formula (II)

the process comprising
(i) providing a mixture comprising formaldehyde and a compound of formula (I)

(ii) contacting the mixture provided in (i) with a condensation catalyst comprising a zeolitic material, obtaining a mixture (ii) comprising the compound of formula (II);
wherein $R_1$, $R_2$ and $R_3$ are independently of each other selected from the group consisting of H, optionally substituted $C_1$-$C_{10}$ alkyl, optionally substituted $C_2$-$C_{10}$ alkenyl, and optionally substituted aryl having from 6 to 12 carbon atoms;
wherein the framework structure of the zeolitic material in (ii) comprises Si, O, optionally Al, and a tetravalent element Y which is one or more of Sn, Ti and Zr, and wherein in the framework structure of the zeolitic material in (ii), the molar ratio Al:Si, calculated as elemental aluminum and silicon, is in the range of from 0:1 to 0.001:1 and wherein the zeolitic material according to (ii) has a desorption maximum within the temperature ranges of from 0 to 250° C., in a temperature-programmed desorption with $NH_3$ as measured according to Reference Example 1.4. Preferably, the compound of formula (II) is a compound of formula (II') and the compound of formula (I) is a compound of formula (I').

Preferably, the zeolitic material according to (ii) comprises, preferably consists of, 10 membered-ring pores, or 12 membered-ring pores, or 10 membered-ring pores and 12 membered-ring pores. Preferably, the framework structure of the zeolitic material according to (ii) comprises, preferably has, the framework type BEA, MFI, MWW, MEL, MEL/MFI, GME, MOR, MTT, MTW, FER, or CON or a mixed structure thereof, or a mixture of these structures. More preferably, the framework structure of the zeolitic material according to (ii) comprises, preferably has, the framework type BEA, or MFI, or MWW or a mixed structure thereof, or a mixture of these structures. More preferably, the framework structure of the zeolitic material according to (ii) comprises, preferably has, the framework type BEA.

Therefore, the present invention preferably relates to a process for preparing compound of formula (II')

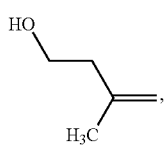

(II')

the process comprising (i) providing a mixture comprising aqueous formaldehyde, a solvent and a compound of formula (I')

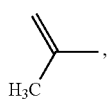

(I')

wherein the molar ratio of the compound of formula (I) relative to formaldehyde, calculated as $CH_2O$, is in the range from 1:1 to 12:1 and wherein the solvent is tert-butanol or a mixture of tert-butanol and water;

(ii) contacting the mixture provided in (i) with a condensation catalyst comprising a zeolitic material, obtaining a mixture comprising the compound of formula (II');

wherein the framework structure of the zeolitic material in (ii) comprises Si, O, optionally Al, and a tetravalent element Y which is one or more of Sn, Ti and Zr, and wherein in the framework structure of the zeolitic material in (ii), the molar ratio Al:Si, calculated as elemental aluminum and silicon, is in the range of from 0:1 to 0.001:1; wherein the zeolitic material in (ii) has a framework type which is one or more of BEA, MFI, and MWW.

According to a preferred embodiment of the present invention, the zeolitic material according to (ii) comprises, preferably has, the framework type BEA. Preferably, Y comprises, more preferably is, Sn.

Therefore, the present invention preferably relates to a process for preparing compound of formula (II')

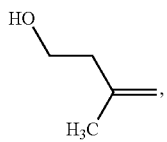

(II')

the process comprising (i) providing a mixture comprising aqueous formaldehyde, a solvent and a compound of formula (I')

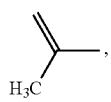

(I')

wherein the molar ratio of the compound of formula (I) relative to formaldehyde, calculated as $CH_2O$, is in the range from 1:1 to 12:1 and wherein the solvent is tert-butanol or a mixture of tert-butanol and water;

(ii) contacting the mixture provided in (i) with a condensation catalyst comprising a zeolitic material having framework type BEA, obtaining a mixture comprising the compound of formula (II');

wherein the framework structure of the zeolitic material in (ii) comprises Si, O, optionally Al, and a tetravalent element Y which is Sn, and wherein in the framework structure of the zeolitic material in (ii), the molar ratio Al:Si, calculated as elemental aluminum and silicon, is in the range of from 0:1 to 0.001:1.

The zeolitic material of framework type BEA preferably comprises Y, more preferably Sn, in an amount in the range of from 1 to 20 weight-%, more preferably in the range of from 2 to 18 weight-%, more preferably in the range of from 3 to 17 weight-%, more preferably in the range of from 4 to 16 weight-%, more preferably in the range of from 10 to 14 weight-% based on the total weight of the zeolitic material. Preferably, the framework structure of framework type BEA, apart from Sn, does not comprise any further tetravalent element Y. Preferred zeolitic materials having framework type BEA and comprising Sn are disclosed in WO 2015/067654 A. These materials are preferably prepared by deboronation of a boron-containing zeolitic material having framework type BEA, followed by introducing the tin into the deboronated material and an acid treatment, wherein the acid treatment is carried out with an aqueous solution having a pH of at most 5.

Thus, a zeolitic material having framework type BEA comprising Sn can be prepared by a process comprising (1) providing a zeolitic material having a BEA framework structure comprising Si and O and Y wherein Y is the tetravalent element Sn, said BEA framework structure having vacant tetrahedral framework sites;

(2) providing a tin-ion source in solid form;

(3) incorporating tin into the zeolitic material provided in (1) by bringing the zeolitic material provided in (1) in contact with the tin-ion source provided in (2) under solid-state ion exchange conditions, obtaining a tin-containing zeolitic material having a BEA framework structure;

(4) subjecting the zeolitic material obtained from (3) to a heat treatment;

(5) treating the heat-treated zeolitic material obtained from (4) with an aqueous solution having a pH of at most 5.

The zeolitic material of (1) can for example be a deboronated zeolitic material having a BEA framework. The preparation of a deboronated zeolitic material having framework type BEA is disclosed in Reference Examples 5 and 6 of WO 2015/067654. The preparation of the tin-containing zeolitic material having a BEA framework is for example disclosed in Comparative Examples 1 to 4 of WO 2015/067654 A, and the acid treatment of the tin-containing zeolitic material having a BEA framework is disclosed in Examples 1 to 4 of WO 2015/067654 A.

Hence, according to the present invention, a preferred zeolitic material having framework type BEA structure type and comprising a tetravalent element Y being Sn, and further comprising B wherein the molar ratio B:Si is preferably in the range of from 0.0018:1 to 0.006:1, wherein preferably at least 99 weight-% of the framework structure of the zeolitic material consist of Si, B, Sn, O and H and wherein the zeolitic material has a water adsorption of preferably at most 12 weight-%, more preferably at most 10 weight-%, determined as described in Reference Example 1.3 herein, and wherein this zeolitic material preferably has an XRD spectrum exhibiting peaks at 2 theta values at (21.5±0.2)°, (22.6±0.2)°, (25.5±0.2)°, (26.6±0.2)°, (28.8±0.2)°, (29.7±0.2)°, (32.2±0.2)°, (34.0±0.2)°, (37.9±0.2)°, determined as described in Reference Example 1.2 herein.

According to a further preferred embodiment of the present invention, the zeolitic material according to (ii) comprises, preferably has, the framework type MFI. Preferably, the zeolitic material comprises Y which is either Zr or a Y is Sn and Ti; therefore, the zeolitic material according to (ii) comprises, preferably has, the framework type MFI and more preferably is one or more of Zr-MFI and Sn—Ti-MFI. Preferably, the framework structure o framework type MFI, apart from Zr or both Sn and Ti, does not comprise any further tetravalent element Y.

Therefore, the present invention preferably relates to a process for preparing compound of formula (II')

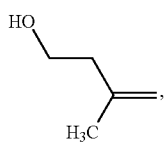

the process comprising
(i) providing a mixture comprising aqueous formaldehyde, a solvent and a compound of formula (I')

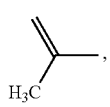

wherein the molar ratio of the compound of formula (I) relative to formaldehyde, calculated as $CH_2O$, is in the range from 1:1 to 12:1 and wherein the solvent is tert-butanol or a mixture of tert-butanol and water;
(ii) contacting the mixture provided in (i) with a condensation catalyst comprising a zeolitic material having framework type MFI, obtaining a mixture comprising the compound of formula (II');
wherein the framework structure of the zeolitic material in (ii) comprises Si, O, optionally Al, and a tetravalent element Y which is Zr or Y is Sn and Ti, and wherein in the framework structure of the zeolitic material in (ii), the molar ratio Al:Si, calculated as elemental aluminum and silicon, is in the range of from 0:1 to 0.001:1.

According to a further preferred embodiment of the present invention, the zeolitic material according to (ii) comprises, preferably has, the framework type MWW. Preferably, the zeolitic material comprises Y which is one of Sn and Ti; therefore, the zeolitic material according to (ii) comprises, preferably has, the framework type MWW and more preferably is one or more of Sn-MWW and Ti-MWW. Preferably, the framework structure of framework type MWW, apart from Sn or Ti, does not comprise any further tetravalent element Y.

Therefore, the present invention preferably relates to a process for preparing compound of formula (II')

the process comprising
(i) providing a mixture comprising aqueous formaldehyde, a solvent and a compound of formula (I')

wherein the molar ratio of the compound of formula (I) relative to formaldehyde, calculated as $CH_2O$, is in the range from 1:1 to 12:1 and wherein the solvent is tert-butanol or a mixture of tert-butanol and water;
(ii) contacting the mixture provided in (i) with a condensation catalyst comprising a zeolitic material having framework type MWW, obtaining a mixture comprising the compound of formula (II');
wherein the framework structure of the zeolitic material in (ii) comprises Si, O, optionally Al, and a tetravalent element Y which is Sn or Ti, and wherein in the framework structure of the zeolitic material in (ii), the molar ratio Al:Si, calculated as elemental aluminum and silicon, is in the range of from 0:1 to 0.001:1.

Generally, it may be conceivable that the zeolitic material according to (ii) could comprise one or more extra-framework elements Z, such as Ti, Zr, V, Nb, Ta, Cr, Mo, W, Mn, Fe, Co, Ni, Zn, Ga, Ge, In, Sn, Pb, P, N, S, Li, Na, K, Rb, Cs, Be, Mg, Ca, Sr, Ca. If a given zeolitic material according to (ii) comprises an extra-framework element, it is preferred that this element is one of the elements constituting the framework, more preferably one or more Ti, Sn and Zr.

It is additionally possible that the condensation catalyst according to (ii) further comprises a binder material in addition to the zeolitic material. Possible binder materials include all materials which are known to those skilled in the art and can be used here as binder material, and which affect the catalyst only to a minor degree or only to the degree of the resulting dilution of the catalyst, if at all.

Preferably, the binder material is one or more of graphite, silica, titania, zirconia, a mixture of one or two thereof, and a mixed oxide of two or more of Si, Ti and Zr, wherein the binder material is preferably one or more of graphite, silica, titania and zirconia, wherein more preferably, the binder material is zirconia or silica. The weight ratio of the zeolitic material in (ii) to the binder material is not subject to any restrictions in principle. In general, the weight ratio of the zeolitic material in (ii) to the binder material may be in the range from 15:1 to 3:1 preferably in the range of from 9:1 to 4:1.

The condensation catalyst according to (ii) may, in addition to the zeolitic material in (ii) and the binder material, also comprise suitable further components. Preferably, at least 50 weight-%, more preferably at least 75 weight-%, more preferably at least 90 weight-%, more preferably at least 95 weight-%, more preferably at least 97 weight-%, more preferably at least 98 weight-%, more preferably at least 99 weight, such as at least 99.5 weight-% or at least 99.9 weight-%, of the condensation catalyst according to (ii) consist of the zeolitic material and optionally the binder.

The condensation catalyst in (ii) may be a shaped catalyst. The condensation catalyst in (ii) may be in any form suitable for the performance of the process according to the invention. Consequently, the condensation catalyst in (ii) may be in powder form, in the form of spray powder, or in the form of spray granules. Equally, the condensation catalyst may be in the form of shaped bodies. If the condensation catalyst is in the form of shaped bodies, it is preferably shaped to rectangular, a triangular, a hexagonal, a square, an oval or a circular cross section, and/or is in the form of a star, a tablet, a sphere, or a hollow cylinder.

According to (ii), the mixture according to (i) is contacted with the condensation catalyst comprising a zeolitic material to obtain the mixture comprising the compound of formula (II). The mixture obtained from (ii) may be present completely in gaseous form, completely in liquid form or in a form in which at least one component is in gaseous form and at least one component in liquid form. Preferably, the mixture of (i) in step (ii) is obtained completely in liquid form.

Preferably, the contacting in (ii) is effected at a temperature of the mixture in the range of from 60 to 150° C., more preferably in the range of from 70 to 115° C., more preferably in the range of from 75 to 105° C. This temperature should be understood as the highest temperature of the liquid phase in the respective reactor used for the reaction in (ii). Preferably, the contacting in (ii) is effected at an absolute pressure of the mixture in the range of from 0.01 to 40 bar(abs), further preferably in the range of from 0.01 to 25 bar(abs), further preferably in the range of from 0.05 to 20 bar(abs). More preferably, the contacting in (ii) is effected at a temperature in the range from 75 to 105° C. and a pressure of 0.05 to 20 bar(abs).

The space velocity (weight hourly space velocity, WHSV) with respect to the contacting in (ii) of the process according to the invention is preferably chosen such that an advantageous balance of conversion, selectivity, yield, reactor geometry, reactor dimensions and process regime is obtained. In the context of the present invention, the weight hourly space velocity is understood to mean mass flow formaldehyde, calculated as $CH_2O$, comprised in the mixture provided in (i) in kg/h divided by the mass of the zeolitic material comprised in the condensation catalyst in kg with which the mixture provided in (i) is contacted in (ii). The space velocity therefore has the unit (1/time). Preferably, the space velocity (weight hourly space velocity, WHSV) in the present process is in the range from 0.1 to 1.0 $h^{-1}$, more preferably from 0.15 to 0.6 $h^{-1}$.

Therefore, the present invention preferably relates to a process for preparing compound of formula (II')

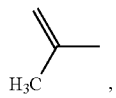
(II')

the process comprising
(i) providing a mixture comprising aqueous formaldehyde, a solvent and a compound of formula (I')

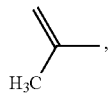
(I')

wherein the molar ratio of the compound of formula (I) relative to formaldehyde, calculated as $CH_2O$, is in the range from 1:1 to 12:1 and wherein the solvent is tert-butanol or a mixture of tert-butanol and water;
(ii) contacting the mixture provided in (i) with a condensation catalyst comprising a zeolitic material at a temperature in the range from 75 to 105° C. and a pressure of 0.05 to 20 bar(abs), obtaining a mixture comprising the compound of formula (II');
wherein the framework structure of the zeolitic material in (ii) comprises Si, O, optionally Al, and a tetravalent element Y which is one or more of Sn, Ti and Zr, and wherein in the framework structure of the zeolitic material in (ii), the molar ratio Al:Si, calculated as elemental aluminum and silicon, is in the range of from 0:1 to 0.001:1.

Therefore, the present invention more preferably relates to a process for preparing compound of formula (II')

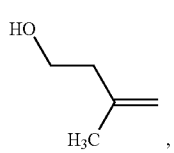
(II')

the process comprising
(i) providing a mixture comprising aqueous formaldehyde, a solvent and a compound of formula (I')

(I')

wherein the molar ratio of the compound of formula (I) relative to formaldehyde, calculated as $CH_2O$, is in the range from 1:1 to 12:1 and wherein the solvent is tert-butanol or a mixture of tert-butanol and water;
(ii) contacting the mixture provided in (i) with a condensation catalyst comprising a zeolitic material at a temperature in the range from 75 to 105° C. and a pressure of 0.05 to 20 bar(abs), obtaining a mixture comprising the compound of formula (II');
wherein the framework structure of the zeolitic material in (ii) comprises Si, O, optionally Al, and a tetravalent element Y which is one or more of Sn, Ti and Zr, and wherein in the framework structure of the zeolitic material in (ii), the molar ratio Al:Si, calculated as elemental aluminum and silicon, is in the range of from 0:1 to 0.001:1;
wherein the zeolitic material in (ii) has a framework type which is one or more of BEA, MFI, and MWW.

More preferably, the present invention more preferably relates to a process for preparing compound of formula (II')

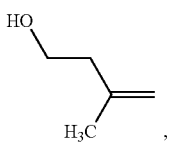

the process comprising
(i) providing a mixture comprising aqueous formaldehyde, a solvent and a compound of formula (I')

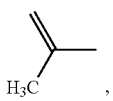

wherein the molar ratio of the compound of formula (I) relative to formaldehyde, calculated as $CH_2O$, is in the range from 1:1 to 12:1 and wherein the solvent is tert-butanol or a mixture of tert-butanol and water;
(ii) contacting the mixture provided in (i) with a condensation catalyst comprising a zeolitic material having framework type BEA at a temperature in the range from 75 to 105° C. and a pressure of 0.05 to 20 bar(abs), obtaining a mixture comprising the compound of formula (II');
wherein the framework structure of the zeolitic material in (ii) comprises Si, O, optionally Al, and a tetravalent element Y which is Sn, and wherein in the framework structure of the zeolitic material in (ii), the molar ratio Al:Si, calculated as elemental aluminum and silicon, is in the range of from 0:1 to 0.001:1.

It has been found that in the process of the present invention, the selectivity is high. It has been found that the selectivity $S_{30}$ of the contacting according to (ii) is at least 35%, preferably at least 40%, more preferably at least 50%, more preferably at least 60%, more preferably at least 70%, wherein the selectivity $S_{30}$ is defined as the selectivity measured after a contacting time in (ii) of 30 h, and wherein the selectivity is defined as the molar amount of the compound of formula (II) comprised in the mixture obtained in (ii) relative to the molar amount of formaldehyde comprised in the mixture provided in (i) and brought into contact with the condensation catalyst according to ((ii).

It has been further found that the selectivity $S_{50}$ of the contacting according to (ii) is at least 35%, preferably at least 40%, more preferably at least 50%, more preferably at least 60%, more preferably at least 70%. The selectivity $S_{50}$ is defined as the selectivity measured after a contacting time in (ii) of 50 h, wherein the selectivity is defined as the molar amount of the compound of formula (II) comprised in the mixture obtained in (ii) relative to the molar amount of formaldehyde comprised in the mixture provided in (i) and brought into contact with the condensation catalyst according to (ii).

It has been further found that the selectivity $S_{100}$ of the contacting according to (ii) is at least 35%, preferably at least 40%, more preferably at least 50%, more preferably at least 60%, more preferably at least 70%. The selectivity $S_{100}$ is defined as the selectivity measured after a contacting time in (ii) of 100 h, wherein the selectivity is defined as the molar amount of the compound of formula (II) comprised in the mixture obtained in (ii) relative to the molar amount of formaldehyde comprised in the mixture provided in (i) and brought into contact with the condensation catalyst according to (ii).

Advantageously the process of the present invention is carried out with a high conversion of formaldehyde. It has been found that the conversion $C_{30}$ of the formaldehyde is at least 80%, preferably at least 90%. The conversion $C_{30}$ is defined as the conversion of the formaldehyde at a contacting time in (ii) after 30 h. The conversion $C_{50}$ of the formaldehyde is at least 80%, preferably at least 90%, wherein the conversion $C_{50}$ is defined as the conversion at a contacting time in (ii) after 50 h. The conversion $C_{100}$ of the formaldehyde is at least 80%, preferably at least 90%, wherein the conversion $C_{100}$ is defined as the conversion of the formaldehyde at a contacting time in (ii) after 100 h.

The process according to the invention may comprise one or more further steps in addition to steps (i) and (ii). For example, the process according to the invention additionally comprises the regenerating of the condensation catalyst used in (ii). In this context, it may be conceivable to regenerate the catalyst at a temperature elevated relative to room temperature in a suitable gas atmosphere for a suitable period of time. Further, the process according to the invention additionally comprises the recycling of the compound of formula (I) which may be present in non-converted form in the mixture obtained from (ii).

The present invention is further directed to a mixture comprising a compound of formula (II)

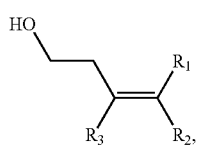

wherein $R_1$, $R_2$ and $R_3$ are as defined above, wherein the mixture is obtainable or obtained by a process as described above.

The present invention is further directed to the use of a zeolitic material as defined above as a catalytically active material for a condensation reaction, preferably as a catalytically active material for an aldehyde/alkene condensation reaction, preferably as a catalytically active material in a Prins condensation reaction, wherein the product of said condensation reaction is preferably a compound of formula (II)

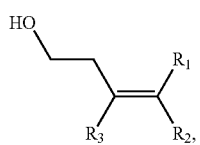

wherein $R_1$, $R_2$ and $R_3$ are as defined above.

The present invention is further directed to the use of a compound of formula (II)

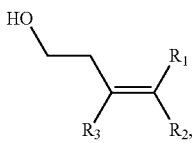

(II)

wherein $R_1$, $R_2$ and $R_3$ are as defined above, wherein the compound of formula (II) is comprised in the mixture obtained from (ii) as described above, as a starting material for preparing a monomeric, oligomeric or polymeric compound, preferably as a starting material for preparing a monomeric, oligomeric or polymeric compound, preferably as a starting material for preparing an aroma chemical, preferably one or more of 3,7-dimethyl-2,6-octadienal (Citral), 2-isobutyl-4-hydroxy-4-methyl tetrahydropropane (Pyranol), or as a starting material for preparing an isoprenol polyether derivative as a component of a copolymer which is suitable as a superplasticizer for a hydraulic binder. Preferably, the compound of formula (II) is used as a starting material for preparing the E-isomer of 3,7-dimethyl-2,6-octadienal (geranial) or the Z-isomer of 3,7-dimethyl-2,6-octadienal (neral) or a mixture of said E-isomer and said Z-isomer, preferably a racemic mixture thereof (citral), wherein one or more thereof are preferably used as an aroma chemical compound. Citral, for example, can be further used as a starting material for preparing terpenic aroma chemicals, for example citronellol, geraniol, or L-menthol. Yet further, citral can be used as a building block in the synthesis if Vitamin A or Vitamin E. With regard to the use as a starting material for preparing Pyranol, reference is made, for example, to the respective disclosure in US 2012059177 A, WO 2011/154330 A and WO 2011/147919 A. With regard to the use as a starting material for preparing an isoprenol polyether derivative, reference is made, for example, to the respective disclosure in US 2011054083 A where such copolymers and their preparation is described, said copolymers comprising 5-55 mol-% of said isoprenol polyether derivative structural unit alpha, 2-90 mol-% of an acrylic acid derivative structural unit beta, and 2-90 mol-% of a hydroxyalkyl acrylate structural unit gamma. Specifically, said isoprenol polyether derivative structural unit alpha is represented by the formula —(CH$_2$—C(CH$_3$)((C$_2$H$_4$—O-(A-O)$_a$—H))— wherein A are as defined in US 2011054083 A.

The present invention is further illustrated by the following set of embodiments and combinations of embodiments resulting from the dependencies and back-references as indicated. In particular, it is noted that in each instance where a range of embodiments is mentioned, for example in the context of a term such as "The process of any one of embodiments 1 to 4", every embodiment in this range is meant to be explicitly disclosed for the skilled person, i.e. the wording of this term is to be understood by the skilled person as being synonymous to "The process of any one of embodiments 1, 2, 3, and 4".

1. A process for preparing a compound of formula (II)

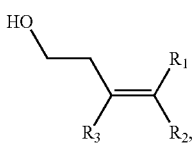

(II)

comprising
(i) providing a mixture comprising formaldehyde and a compound of formula (I)

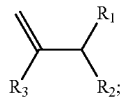

(I)

(ii) contacting the mixture provided in (i) with a condensation catalyst comprising a zeolitic material, obtaining a mixture (ii) comprising the compound of formula (II); wherein $R_1$, $R_2$ and $R_3$ are independently of each other selected from the group consisting of H, optionally substituted $C_1$-$C_{10}$ alkyl, optionally substituted $C_2$-$C_{10}$ alkenyl and optionally substituted aryl having from 6 to 12 carbon atoms; and
wherein the framework structure of the zeolitic material in (ii) comprises Si, O, optionally Al, and a tetravalent element Y other than Si, preferably one or more of Sn, Ti, Zr, and Ge, more preferably one or more of Sn, Ti and Zr, wherein in the framework structure of the zeolitic material in (ii), the molar Al:Si ratio is in the range of from 0:1 to 0.001:1.

2. The process of embodiment 1, wherein Y is Sn.
3. The process of embodiment 1, wherein Y is Zr, or wherein Y is Sn and Ti, or wherein Y is Sn and Ti and Zr.
4. The process of any of embodiments 1 to 3, wherein the NH$_3$ desorption maximum of the zeolitic material according to (ii) exhibited in the temperature-programmed desorption with NH$_3$ according to the NH$_3$-TPD method as described in Reference Example 1.4 herein is in the temperature range of from 0 to 250° C., wherein in said temperature-programmed desorption with NH$_3$, the zeolitic material according to (ii) preferably does not exhibit an NH$_3$ desorption at a temperature above 250° C.
5. The process of any one of embodiments 1 to 4, wherein in the framework structure of the zeolitic material in (ii), the molar Al:Si ratio, calculated as elemental aluminum and silicon, is in the range of from 0:1 to 0.0001:1, preferably in the range of from 0:1 to 0.00001:1.
6. The process of any one of embodiments 1 to 5, wherein at least 99 weight-% of the framework structure of the zeolitic material in (ii) consists of Si, Y, O and H.
7. The process of any one of embodiments 1 to 6, where the framework structure of the zeolitic material in (ii) comprises Y in an amount of from 1 to 20 weight-%, preferably in the range of from 2 to 18 weight-%, more preferably in the range of from 3 to 17 weight-%, more preferably in the range of from 4 to 16 weight-%, based on the total weight of the zeolitic material.
8. The process of any one of embodiments 1 to 7, wherein the framework structure of the zeolitic material in (ii) further comprises no trivalent element X other than optionally Al.
9. The process of any one of embodiments 1 to 8, wherein the zeolitic material in (ii) comprises, preferably consists of, 10 membered-ring pores, or 12 membered-ring pores, or 10 membered-ring pores and 12 membered-ring pores.
10. The process of any one of embodiments 1 to 9, wherein the framework structure of the zeolitic material in (ii) has framework type BEA, MFI, MWW, MEL, MEL/MFI, GME, MOR, MTT, MTW, FER, or CON, preferably BEA, MFI, MWW or a mixed structure thereof.

11. The process of any one of embodiments 1 to 10, wherein the framework structure of the zeolitic material in (ii) has framework type BEA.
12. The process of embodiment 11, wherein the tetravalent element Y comprised in the zeolitic framework structure is one or more of Sn and Zr, preferably is Sn.
13. The process of embodiment 12, wherein the zeolitic material comprises Sn in an amount in the range of from 2 to 20 weight-%, preferably in the range of from 5 to 18 weight-%, more preferably in the range of from 8 to 16 weight-%, more preferably in the range of from 10 to 14 weight-% based on the total weight of the zeolitic material.
14. The process of any one of embodiment 11 to 13, wherein the zeolitic framework comprises B and the molar B:Si ratio, calculated as elemental boron and silicon, is at most 0.04:1, preferably at most 0.02:1, more preferably in the range of from 0.0010:1 to 0.02:1, more preferably in the range of from 0.0018:1 to 0.006:1.
15. The process of any one of embodiments 11 to 14, wherein the zeolitic material has a water adsorption of at most 12 weight-%, preferably at most 10 weight-%, determined as described in Reference Example 1.3 herein.
16. The process of any one of embodiments 11 to 15, wherein the zeolitic material has an XRD spectrum exhibiting peaks at 2 theta values at $(21.5\pm0.2)°$, $(22.6\pm0.2)°$, $(25.5\pm0.2)°$, $(26.6\pm0.2)°$, $(28.8\pm0.2)°$, $(29.7\pm0.2)°$, $(32.2\pm0.2)°$, $(34.0\pm0.2)°$, $(37.9\pm0.201°)$, determined as described in Reference Example 1.2 herein.
17. The process of any one of embodiments 1 to 10, wherein the framework structure of the zeolitic material in (ii) has framework type MFI.
18. The process of embodiment 17, wherein Y is Zr, or wherein Y is Sn and Ti, or wherein Y is a Sn and Ti and Zr.
19. The process of any one of embodiments 1 to 10, wherein the framework structure of the zeolitic material in (ii) has framework type MWW.
20. The process of embodiment 19, wherein Y is Sn or Ti.
21. The process of any one of embodiments 1 to 20, wherein the condensation catalyst in (ii) is in the form of a shaped body.
22. The process of embodiment 21, wherein the shaped body has a rectangular, a triangular, a hexagonal, a square, an oval or a circular cross section, and/or is in the form of a star, a tablet, a sphere, or a hollow cylinder.
23. The process of any one of embodiments 1 to 22, wherein the condensation catalyst in (ii) comprises a binder material in addition to the zeolitic material.
24. The process of embodiment 23, wherein the binder material is one or more of graphite, silica, titania, zirconia, and a mixed oxide of two or more of Si, Ti and Zr, wherein the binder material is preferably one or more of graphite, silica, titania and zirconia, wherein more preferably, the binder material is zirconia or silica.
25. The process of embodiment 23 or 24, wherein in the condensation catalyst, the weight ratio of the zeolitic material relative to the binder material is in the range of from 15:1 to 3:1, preferably in the range of from 9:1 to 4:1.
26. The process of any one of embodiments 1 to 22, wherein the condensation catalyst in (ii) comprises the zeolitic material in an amount of at least 90 weight-%, preferably of at least 95 weight-%, more preferably of at least 99 weight-%, more preferably of at least 99.5 weight-%, more preferably of at least 99.9 weight-%, based on the total weight of the condensation catalyst.
27. The process of any one of embodiments 1 to 26, wherein the formaldehyde in (i) is one or more of aqueous formaldehyde, trioxane and paraformaldehyde, wherein the formaldehyde is preferably aqueous formaldehyde.
28. The process of embodiment 27, wherein the aqueous formaldehyde comprises the formaldehyde, calculated as $CH_2O$, in an amount in the range of from 30 to 80 weight-%, or in the range of from 45 to 75 weight-%, or in the range of from 60 to 70 weight-%, based on the total weight of the aqueous formaldehyde.
29. The process of any one of embodiments 1 to 28, wherein in the mixture provided in (i), the molar ratio of the compound of formula (I) relative to the formaldehyde, calculated as $CH_2O$, is in the range from 1:1 to 12:1, preferably in the range of from 5:1 to 11.5:1, more preferably in the range of from 9:1 to 10:1.
30. The process of any one of embodiments 1 to 29, wherein contacting the mixture provided in (i) with the condensation catalyst according to (ii) is carried out in a batch mode or in a semi-continuous mode or in a continuous mode, preferably in a continuous mode.
31. The process of any one of embodiments 1 to 30, wherein the mixture provided in (i) is contacted with the condensation catalyst according to (ii) in liquid phase.
32. The process of any one of embodiments 1 to 31, wherein the mixture provided in (i) is provided in liquid form.
33. The process of embodiment 32, wherein prior to (ii), the mixture provided in (i) is brought to a temperature in the range from 50 to 150° C., preferably in the range of from 80 to 120° C., more preferably in the range of from 95 to 110° C.
34. The process of embodiments 32 or 33, wherein the contacting in (ii) is carried out at a temperature of the mixture brought in contact with the condensation catalyst in the range of from 60 to 150° C., preferably in the range of from 70 to 115° C., more preferably in the range of from 75 to 105° C.
35. The process of any one of embodiments 32 to 34, wherein the contacting in (ii) is carried out at a pressure of the mixture brought in contact with the condensation catalyst in the range of from 0.01 to 40 bar(abs), preferably from 0.01 to 25 bar(abs), more preferably in the range of from 0.05 to 20 bar(abs).
36. The process of any one of embodiments 1 to 35, wherein the contacting in (ii) is carried out at a weight hourly space velocity in the range of from 0.1 to 1.0 $h^{-1}$, preferably in the range of from 0.15 to 0.6 $h^{-1}$, wherein the weight hourly space velocity is defined as the mass flow rate of the formaldehyde, calculated as $CH_2O$ comprised in the mixture provided in (i) in kg/h divided by the mass of the zeolitic material comprised in the condensation catalyst in kg with which the mixture provided in (i) is contacted in (ii).
37. The process of any one of embodiments 1 to 36, wherein the mixture in provided in (i) additionally comprises a solvent, wherein the solvent is preferably one or more of 3-methyl-2-buten-1-ol (prenol), ethylhexanol, methanol, acetonitrile, ethylacetate, tert-butanol, water and acetone, more preferably one or more of water, tert-butanol and ethylacetate, wherein more preferably, the solvent is tert-butanol or a mixture of tert-butanol and water.
38. The process of any one of embodiments 1 to 37, further comprising separating the compound of formula (II) from the mixture obtained in (ii).
39. The process of any one of embodiments 1 to 38, wherein the mixture obtained in (ii) further comprises the compound of formula (I), the process further comprising recycling, preferably recycling to the process according to any one of embodiments 1 to 38, the compound of formula (I).

40. The process of any one of embodiments 1 to 39, further comprising regenerating the condensation catalyst according to (ii).

41. The process of any one of embodiments 1 to 40, wherein $R_1$ and $R_2$ are each H and $R_3$ is $C_1$-$C_{10}$ alkyl.

42. The process of any one of embodiments 1 to 41, wherein $R_1$ and $R_2$ are each H and $R_3$ is $CH_3$.

43. The process of any one of embodiments 1 to 42, wherein the selectivity $S_{30}$ of the contacting according to (ii) is at least 35%, preferably at least 40%, more preferably at least 50%, more preferably at least 60%, more preferably at least 70%, wherein the selectivity $S_{30}$ is defined as the selectivity measured after a contacting time in (ii) of 30 h, wherein the selectivity is defined as the molar amount of the compound of formula (II) comprised in the mixture obtained in (ii) relative to the molar amount of formaldehyde comprised in the mixture provided in (i) and brought into contact with the condensation catalyst according to ((ii).

44. The process of any one of embodiments 1 to 43, wherein the selectivity $S_{50}$ of the contacting according to (ii) is at least 35%, preferably at least 40%, more preferably at least 50%, more preferably at least 60%, more preferably at least 70%, wherein the selectivity $S_{50}$ is defined as the selectivity measured after a contacting time in (ii) of 50 h, wherein the selectivity is defined as the molar amount of the compound of formula (II) comprised in the mixture obtained in (ii) relative to the molar amount of formaldehyde comprised in the mixture provided in (i) and brought into contact with the condensation catalyst according to (ii).

45. The process of any one of embodiments 1 to 44, wherein the selectivity $S_{100}$ of the contacting according to (ii) is at least 35%, preferably at least 40%, more preferably at least 50%, more preferably at least 60%, more preferably at least 70%, wherein the selectivity $S_{100}$ is defined as the selectivity measured after a contacting time in (ii) of 100 h, wherein the selectivity is defined as the molar amount of the compound of formula (II) comprised in the mixture obtained in (ii) relative to the molar amount of formaldehyde comprised in the mixture provided in (i) and brought into contact with the condensation catalyst according to (ii).

46. The process of any one of embodiments 1 to 45, wherein the conversion $C_{30}$ of the formaldehyde is at least 80%, preferably at least 90%, wherein the conversion $C_{30}$ is defined as the conversion at a contacting time in (ii) of 30 h.

47. The process of any one of embodiments 1 to 46, wherein the conversion $C_{50}$ of the formaldehyde is at least 80%, preferably at least 90%, wherein the conversion $C_{50}$ is defined as the conversion at a contacting time in (ii) of 50 h.

48. The process of any one of embodiments 1 to 47, wherein the conversion $C_{100}$ of the formaldehyde is at least 80%, preferably at least 90%, wherein the conversion $C_{100}$ is defined as the conversion at a contacting time in (ii) of 100 h.

49. A process for preparing 3-methyl-3-buten-1-ol, preferably the process of any one of embodiments 1 to 48, comprising
(i) providing a mixture comprising formaldehyde and 2-methylpropene;
(ii) contacting the mixture the provided in (i) with a condensation catalyst comprising a zeolitic material, obtaining a mixture (ii) comprising 3-methyl-3-buten-1-ol;

wherein at least 99 weight-%, preferably at least 99.9 weight-%, more preferably at least 99.99 weight-% of the framework structure of the zeolitic material in (ii) consist of Si, a tetravalent element Y other than Si, preferably one or more of Sn, Ti, Zr, and Ge, more preferably one or more of Sn, Ti and Zr, O and H.

50. The process of embodiment 49, wherein Y is Sn.

51. The process of embodiment 49 or 50, wherein the framework structure of the zeolitic material in (ii) has framework type BEA.

52. The process of any one of embodiments 49 to 51, wherein the formaldehyde in (i) is aqueous formaldehyde and wherein the aqueous formaldehyde comprises the formaldehyde, calculated as $CH_2O$, in an amount in the range of from 30 to 80 weight-%, or in the range of from 45 to 75 weight-%, or in the range of from 60 to 70 weight-%, based on the total weight of the aqueous formaldehyde.

53. The process of any one of embodiments 49 to 52, wherein the contacting the mixture provided in (i) with the condensation catalyst according to (ii) is carried out in a continuous mode.

54. The process of any one of embodiments 49 to 53, wherein the mixture provided in (i) is provided in liquid form.

55. The process of any one of embodiments 49 to 54, further comprising separating 3-methyl-3-buten-1-ol from the mixture obtained in (ii).

56. The process of any one of embodiments 49 to 55, wherein the mixture obtained in (ii) further comprises 2-methylpropene, the process further comprising recycling the 2-methylpropene, preferably recycling 2-methylpropene to the process according to any one of embodiments 49 to 55.

57. The process of any one of embodiments 49 to 56, further comprising regenerating the condensation catalyst according to (ii).

58. A mixture comprising a compound of formula (II)

obtainable or obtained by a process according to any one of embodiments 1 to 57, preferably according to any one of embodiments 49 to 57.

59. Use of a zeolitic material as defined according to any one of embodiments 1 to 20 as a catalytically active material for a condensation reaction, preferably as a catalytically active material for an aldehyde/alkene condensation reaction, preferably as a catalytically active material in a Prins condensation reaction, wherein the product of said condensation reaction is preferably a compound of formula (II)

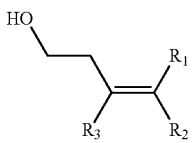

(II)

as defined according to any one of embodiments 1, 41 or 42, more preferably is 3-methyl-3-buten-1-ol.
60. Use of a compound of formula (II)

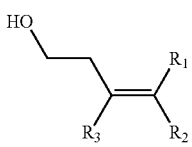

(II)

as defined in any one of embodiments 1, 41 or 42, preferably 3-methyl-3-buten-1-ol, comprised in the mixture obtained in (ii) as defined in any one of embodiments 1 to 58, as a starting material for preparing a monomeric, oligomeric or polymeric compound, preferably as a starting material for preparing an aroma chemical, preferably one or more of 3,7-dimethyl-2,6-octadienal (Citral), 2-isobutyl-4-hydroxy-4-methyl tetrahydropropane (Pyranol), or as a starting material for preparing an isoprenol polyether derivative as a component of a copolymer which is suitable as a superplasticizer for a hydraulic binder.
61. The use of embodiment 60 for preparing the E-isomer of 3,7-dimethyl-2,6-octadienal (Geranial) or the Z-isomer of 3,7-dimethyl-2,6-octadienal (Neral) or a mixture of said E-isomer and said Z-isomer, preferably a racemic mixture thereof (Citral), wherein one or more thereof are preferably used as an aroma chemical compound.
62. The process of any one of embodiments 1 to 57, wherein the mixture provided in (i) and contacted with the condensation catalyst in (ii) contains acetic acid in an amount in the range of from 0 to 500 weight-ppm, preferably in the range of from 0 to 250 weight-ppm, more preferably in the range of from 0 to 100 weight-ppm, wherein more preferably, the mixture provided in (i) and contacted with the condensation catalyst in (ii) does not comprise acetic acid.

The present invention is further illustrated by the following reference examples, examples, and comparative examples.

EXAMPLES

Reference Example 1: Analytical Methods

Reference Example 1.1: Analysis of the Mixture Obtained in (II): Compound of Formula (II) and Formaldehyde The product of formula (II) was quantified by Gas Chromatography weight-% calibrated:
GC-system: Agilent 5890 Series II;
GC-Column: DB-WAX (30 m (length), 0.32 mm (ID), 0.25 micrometer (film));
Temperature program: 35° C. for 7 minutes, 35° C. to 230° C. at 6 K/min.

The unreacted free formaldehyde in the mixture obtained in (ii) was photometrically quantified according the following reaction of formaldehyde with acetylacetone and $NH_4^+$:

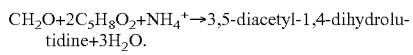

The concentration of the then obtained 3,5-diacetyl-1,4-dihydrolutidine is equivalent to the concentration of formaldehyde and was measured at a wavelength of 412 nm.

Reference Example 1.2: Determination of the Crystallinity of the Zeolitic Material of Reference Example 2.1

The crystallinity of the zeolitic materials of Reference Example 2.1 was determined by XRD analysis using the EVA method as described in the User Manual DIFFRAC.EVA Version 3, page 105, from Bruker AXS GmbH, Karlsruhe.

The respective data were collected on a standard Bruker D8 Advance Diffractometer Series II using a Sol-X detector, from 2° to 50° 2theta, using variable slits (V20), a step size of 0.02° 2theta and a scan speed of 2.4 s/step. Default parameters were used for estimating the background/amorphous content (Curvature=1, Threshold=1).

Reference Example 1.3: Determination of the Water Adsorption of the Zeolitic Material Water adsorption/desorption isotherms were performed on a VTI SA instrument from TA Instruments following a step-isotherm program. The experiment consisted of a run or a series of runs performed on a sample material that has been placed on the microbalance pan inside of the instrument. Before the measurement was started, the residual moisture of the sample was removed by heating the sample to 100° C. (heating ramp of 5° C./min) and holding it for 6 h under a nitrogen flow. After the drying program, the temperature in the cell was decreased to 25° C. and kept isothermal during the measurement. The microbalance was calibrated, and the weight of the dried sample was balanced (maximum mass deviation 0.01 weight-%). Water uptake by the sample was measured as the increase in weight over that of the dry sample. First, as adsorption curve was measured by increasing the relative humidity (RH) (expressed as weight-% water in the atmosphere inside of the cell) to which the sample was exposed and measuring the water uptake by the sample as equilibrium. The RH was increased with a step of 10 weight-% from 5% to 85% and at each step the system controlled the RH and monitored the sample weight until reaching the equilibrium conditions after the sample was exposed from 85 weight-% to 5 weight-% with a step of 10% and the change in the weight of the sample (water uptake) was monitored and recorded.

Reference Example 1.4: Temperature Programmed Desorption of Ammonia ($NH_3$-TPD)

The temperature-programmed desorption of ammonia ($NH_3$-TPD) was conducted in an automated chemisorption analysis unit (Micromeritics AutoChem II 2920) having a thermal conductivity detector. Continuous analysis of the desorbed species was accomplished using an online mass spectrometer (OmniStar QMG200 from Pfeiffer Vacuum). The sample (0.1 g) was introduced into a quartz tube and analysed using the program described below. The temperature was measured by means of an Ni/Cr/Ni thermocouple immediately above the sample in the quartz tube. For the analyses, He of purity 5.0 was used. Before any measurement, a blank sample was analysed for calibration.

1. Preparation: Commencement of recording; one measurement per second. Wait for 10 minutes at 25° C. and a He flow rate of 30 cm³/min (room temperature (about 25° C.) and 1 atm); heat up to 600° C. at a heating rate of 20 K/min; hold for 10 minutes. Cool down under a He flow (30 cm³/min) to 100° C. at a cooling rate of 20 K/min (furnace ramp temperature); Cool down under a He flow (30 cm³/min) to 100° C. at a cooling rate of 3 K/min (sample ramp temperature).
2. Saturation with $NH_3$: Commencement of recording; one measurement per second. Change the gas flow to a mixture of 10% $NH_3$ in He (75 cm³/min; 100° C. and 1 atm) at 100° C.; hold for 30 minutes.
3. Removal of the excess: Commencement of recording; one measurement per second. Change the gas flow to a He flow of 75 cm³/min (100° C. and 1 atm) at 100° C.; hold for 60 min.
4. $NH_3$-TPD: Commencement of recording; one measurement per second. Heat up under a He flow (flow rate: 30 cm³/min) to 600° C. at a heating rate of 10 K/min; hold for 30 minutes.
5. End of measurement.

Desorbed ammonia was measured by means of the online mass spectrometer, which demonstrates that the signal from the thermal conductivity detector was caused by desorbed ammonia. This involved utilizing the m/z=16 signal from ammonia in order to monitor the desorption of the ammonia. The amount of ammonia adsorbed (mmol/g of sample) was ascertained by means of the Micromeritics software through integration of the TPD signal with a horizontal baseline.

Reference Example 2: Preparation of Zeolitic Materials 2.1 Preparation of a Zeolitic Material Having Framework Type BEA and Comprising Sn (Sn-BEA)
a) Preparation of Sn-BEA-Zeolite
Materials used:

| | |
|---|---|
| 50 g | Deboronated BEA-zeolite, spray dried (prepared according to Example 1(ii) of WO 2014/060259) |
| 14.2 g | Sn(OAc)₂ (tin(II)acetate) from Aldrich |

50 g of deboronated BEA zeolite and 14.2 g Sn(OAc)₂ were combined in the laboratory mixer and were ground for 15 min. The obtained mixture was then calcined in a muffle furnace by raising the temperature at the rate of 2 K/min to 500° C. for 3 h. 55.5 g of the zeolite of a) were obtained.
b) Acid Treatment
Materials used:

| | |
|---|---|
| 55 g | Sn-BEA zeolite according to a) |
| 1650 g | HNO₃ 30% aqueous solution |

761.5 g of a solution of 65% HNO₃ were added to a stirred 2 L vessel charged with 888.5 g of deionized water. Under continuous stirring, 55 g of the zeolite according to a) were added to the mixture. The obtained suspension was heated to 100° C. and refluxed for 20 h. The suspension was then cooled, filtered and washed with distilled water until neutral pH (<100 microSiemens). The filtered zeolite was then calcined in the muffle furnace by raising the temperature at the rate of 3 K/min to 120° C. for 10 h followed by raising the temperature at the rate of 2 K/min to 550° C. for 10 h. 52.8 g of the zeolite of b) were obtained.
c) Preparation of a Molding
Materials used:

| | |
|---|---|
| 60 g | Sn-BEA zeolite of b) |
| 17.37 g | ZrOH(OAc)₃ (~10% ZrO₂) from Aldrich |
| 3 g | Walocel ® Wolf Walsrode AG PUFAS Werk KG |
| 53 mL | DI water |

60 g of Sn-BEA zeolite of b), 17.37 g of ZrOH(OAc)₃ and 3 g of Walocel® were combined and mixed in a kneader. 53 mL of deionized water were then added to the mixture which was kneaded until combined. The total kneading time was 30 min. The obtained zeolite was then calcined in the muffle furnace by raising the temperature at the rate of 3 K/min to 120° C. for 6 h followed by raising the temperature at the rate of 2 K/min to 550° C. for 5 h under air. 52.8 g of the molding with a bulk density of 440 g/L were obtained.

2.2 Preparation of a Zeolitic Material Having Framework Type MFI and Comprising Zr (Zr-MFI)
a) Preparation of Zeolite
Materials used:

| | |
|---|---|
| 568.75 g | tetraethyl orthosilicate (TEOS) |
| 30.87 g | Zr(IV)propoxide (70% solution in 1-propanol) |
| 500 g | tetrapropylammonium hydroxide (TPAOH) |
| 500 g | DI water |

30.87 g of Zr(IV) propoxide were added dropwise over 30 min to a vessel charged with 568.75 g of TEOS. 500 g of TPAOH and 500 g of distilled water were added to the mixture which was then stirred for an additional 1 h. 407 g of accrued alcohol were distilled off from the mixture at 95° C. The resulting mixture was then cooled to room temperature. The sol was then diluted with 407 g of DI water. The resulting mixture was then crystallized at 175° C. for 48 h. The sol was diluted 1:1 with distilled water and adjusted to pH 7.5 with 5% HNO₃ solution. The solids were centrifuged. The resulting zeolite was dried at 110° C. for 24 h followed by calcination by raising the temperature at the rate of 2 K/min to 500° C. for 5 h. 128 g of the Zr-MFI zeolite of a) were obtained.
b) Preparation of Molding
Materials used:

| | |
|---|---|
| 50 g | Zr-MFI: zeolite according to a) |
| 22.06 g | 15% SiO₂ on zeolite (Ludox AS-40) |
| 2.5 g | Walocel ® Wolf Walsrode AG PUFAS Werk KG |
| 50 mL | DI water |

50 g of Zr-MFI according to a), 22.06 g of 15% SiO₂ of zeolite and 2.5 g of Walocel® were combined and mixed in a kneader for 10 min. 50 ml of distilled water were then added to the mixture which was kneaded until combined. The total kneading time was 30 min. The obtained zeolite was then calcined in the muffle furnace by raising the temperature at the rate of 3 K/min to 120° C. for 7 h followed by raising the temperature at the rate of 2 K/min to 500° C. for 2 h. 40.3 g of the molding with bulk density of 320 g/L were obtained.

c) Water Treatment

Materials used:

| | |
|---|---|
| 30 g | molding according to b) |
| 600 mL | DI water |

The molding was suspended in DI water and heated at 145° C. for 8 h. The suspension was filtered. The zeolite was then dried at 120° C. for 12 h and calcined by raising the temperature at the rate of 2 K/min to 450° C. for 2 h. 39.3 g of the molding with bulk density of 300 g/L were obtained.

2.3 Preparation of a Zeolitic Material Having Framework Type MFI and Comprising Sn and Ti (Sn-TiMFI)

a) Preparation of Zeolite

Materials used:

| | |
|---|---|
| 575.5 g | tetraethyl orthosilicate (TEOS) |
| 1.6 g | tin (IV) isopropoxide |
| 12.0 g | tetraethyl titanate (TETi) |
| 505.9 g | tetrapropylammonium hydroxide (TPAOH) |
| 505.9 g | DI water |

575.5 g of (TEOS) and 1.6 g of Tin (IV) isopropoxide were stirred together in a vessel for 10 min. Under continuous stirring 12.0 g of TETi were added dropwise and the mixture was then stirred for another 20 min. 505.9 g of TPAOH and 505.9 g of DI water were added to the mixture which was then stirred for an additional 1 h. 369 g of accrued alcohol were distilled off from the mixture at 95° C. The resulting mixture was then cooled to the room temperature. The sol was then diluted with 369 g of purified water. The resulting mixture was then crystallized at 175° C. for 48 h. The sol was diluted 1:1 with DI water and adjusted to pH 7.5 with 10% $HNO_3$ solution. The solid was filtered off and the resulting zeolite was dried at 110° C. for 24 h followed by calcination by raising the temperature at the rate of 2 K/min to 550° C. for 5 h. 168.4 g of the zeolite of a) were obtained.

b) Preparation of the Molding

Materials used:

| | |
|---|---|
| 60 g | Sn—Ti-MFI according to a) |
| 16.67 g | (10% $SiO_2$ on zeolite) Ludox ® AS-40 |
| 3 g | Walocel ® (Wolf Walsrode AG PUFAS Werk KG) |
| 40 mL | DI water |

60 g of the zeolite Sn—Ti-MFI according to a), 16.67 g of Ludox® and 3 g of Walocel® were combined and mixed in a kneader for 10 min. 40 mL of purified water were then added to the mixture which was kneaded until combined. The total kneading time was 30 min. The obtained molding was then calcined in the muffle furnace by raising the temperature at the rate of 3 K/min to 120° C. for 7 h followed by raising the temperature at the rate of 2 K/min to 500° C. for 2 h. 47.2 g of the molding with bulk density of 525 g/L were obtained.

2.4 Preparation of a Zeolitic Material Having Framework Type MWW and Comprising Ga (Ga-MWW)

a) Preparation of a Zeolite

Materials used:

| | |
|---|---|
| 40 g | MWW zeolite prepared according to example 1 of WO 2014/060261 |
| 2 g | $Ga(OMe)_3$ |

A laboratory mixer was prepared for the reaction by being purged with $N_2$ for 30 min. Under $N_2$ atmosphere 40 g of the zeolite and 2 g of $Ga(OMe)_3$ were combined in the prepared laboratory mixer and were ground for 5 min on a middle speed (speed 4). The obtained mixture was dried at 120° C. and then calcined in a muffle furnace by raising the temperature at the rate of 2 K/min to 500° C. for 5 h. 39.4 g of the zeolite of a) were obtained.

b) Preparation of the Molding

Materials used:

| | |
|---|---|
| 30 g | Ga-MWW zeolite according to a) |
| 18.75 g | (20% $SiO2$ on zeolite) Ludox ® AS-40 |
| 1.5 g | Walocel ® (Wolf Walsrode AG PUFAS Werk KG) |
| 65 mL | DI water |

30 g of Ga-MWW zeolite according to a), 18.75 g of 20% $SiO_2$ on zeolite and 1.5 g of Walocel® were combined and mixed in a kneader for 10 min. 65 ml of DI water were then added to the mixture which was kneaded until combined. The total kneading time was 60 min. The obtained zeolite was then calcined in the muffle furnace by raising the temperature at the rate of 3 K/min to 120° C. for 7 h followed by raising the temperature at the rate of 2 K/min to 500° C. for 2 h. 25.3 g of the molding with bulk density of 250 g/L were obtained.

c) Water Treatment

Materials used:

| | |
|---|---|
| 20 g | Ga-MWW zeolite according to b) |
| 400 mL | DI water |

The molding was suspended in DI water and heated at 145° C. for 8 h. The suspension was filtered. The zeolite was then dried at 120° C. for 12 h and calcined by raising the temperature at the rate of 2 K/min to 450° C. for 2 h. 20 g of the molding with a bulk density of 240 g/L were obtained.

2.5 Preparation of a Zeolitic Material Having Framework Type MFI and Comprising Ga (Ga-MFI)

a) Preparation of a Zeolite

Materials used:

| | |
|---|---|
| 272 g | Tetraethyl orthosilicate (TEOS) |

Solution 1:

| | |
|---|---|
| 8.4 g | Natrium hydroxide pellets |
| 272 g | DI water |
| 106.1 g | 40% tetrapropylammonium hydroxide |

Solution 2:

| 6.7 g | Ga(NO$_3$)$_3$ xH$_2$O |
|---|---|
| 68 g | DI water |

A 100 mL dropping funnel was charged with solution 1 and a 500 mL dropping funnel was charged with solution 2. Solution 1 and solution 2 were added dropwise at the same time to a vessel charged with 272 g of TEOS. After 10 min two phases were observed. After 20 min addition of solution 2 ended at 27° C. and 3 min after that the addition of solution 1 ended at 28° C. The resulting mixture was then stirred for 2 h. After additional 5 min a gel was formed. The temperature of the mixture rose to 40° C. in 35 min, and then was cooled off. An autoclave was charged with the gel and was heated at 180° C. for 72 h. The resulting solid was filtered with a black band filter and washed with DI water. The solid was dried overnight at room temperature. The resulting zeolite was then calcined by raising the temperature at a rate of 2 K/min to 540° C. and 10 h at 550° C. under air. 70 g of the zeolite of a) were obtained.

b) Ion Exchange
Materials used:

| 585 g | DI water |
|---|---|
| 65 g | 99% ammonium nitrate (NH$_4$NO$_3$) |
| 65 g | Ga-MFI according to a) |

585 g of DI water and 65 g of 99% ammonium nitrate (NH$_4$NO$_3$) were combined to form a 10% solution. Under continuous stirring 65 g of the Ga-MFI zeolite according to a) were added to the mixture. The obtained mixture was heated to 80° C. and stirred for 2 h. The suspension was then cooled and stirring stopped. After settling, the supernatant solution was removed. A fresh ammonium nitrate solution (10%) was added to the remaining solids and the procedure was repeated. The suspension was then filtered off and washed with DI water. The filtered zeolite was dried at 120° C. for 4 h and then calcined at 500° for 5 h. The temperature program used was: 60 min to 120° C.; 240 min at 120° C.; 190 min to 500° C.; 300 min at 500° C. Air was used as medium. The ion exchange was repeated one more time. The zeolite was dried at 120° C. for 4 h and then calcined at 500° C. for 5 h. The temperature program used was: 60 min to 120° C.; 240 min at 120° C.; 190 min to 500°; 300 min at 500° C.

Air was used as medium. 61 g of the zeolite of b) were obtained.

c) Preparation of Molding
Materials used:

| 40 g | Ga-MFI zeolite according to b) |
|---|---|
| 17.65 g | (15% SiO$_2$ on zeolite) Ludox ® AS-40 |
| 2 g | Walocel ® (Wolf Walsrode AG PUFAS Werk KG) |
| 29 mL | DI water |

40 g of Ga-MFI according to b), 17.65 g of (15% SiO$_2$ on zeolite) and 2 g of Walocel® were combined and mixed in a kneader for 10 min. 29 ml of DI water were then added to the mixture which was kneaded until combined. The total kneading time was 30 min. The obtained zeolite was then calcined in the muffle furnace by raising the temperature at the rate of 3 K/min to 120° C. for 7 h followed by raising the temperature at the rate of 2 K/min to 500° C. for 2 h. 34.2 g of the molding with bulk density of 410 g/L were obtained.

d) Water Treatment
Materials used:

| 30 g | the molding according to c) |
|---|---|
| 600 mL | DI water |

The molding was suspended in DI water and heated at 145° C. for 8 h. The suspension was filtered. The zeolite was then dried at 120° C. for 12 h and calcined by raising the temperature at the rate of 2 K/min to 450° C. for 2 h. 30.8 g of the molding with bulk density of 410 g/L were obtained.

2.6 Preparation of a Zeolitic Material Having Framework Type MFI/MEL and Comprising Fe and (Fe-MFI/MEL)

a) Preparation of the Zeolite 273 kg sodium silicate were provided in a vessel. Under stirring at 100 rpm (rounds per minute), 252.8 kg of hexamethylenediamine solution (56.6 wt.-%) were added and the reactor temperature was raised to 50° C. To the resulting solution, a solution containing: 425 kg de-ionized water, 20.64 kg sulfuric acid (96 wt. %) and 31.1 kg Fe$_2$(SO$_4$)$_3$×H$_2$O was added. The resulting mixture was stirred at 162 rpm for 17 h. The finally obtained mixture was heated to 160° C. within 4 h under autogenous pressure and under stirring (30 rpm). The temperature of 160° C. was kept essentially constant for 94 h; during these 94 h, the mixture was stirred at 18 rpm. Subsequently, the mixture was cooled to a temperature of 40° C. within 2 h. After cooling the zeolite material was separated by filtration using a suction filter. The filter cake was washed with de-ionized water until the washing water had a conductivity of less than 300 microSiemens/cm. The filter cake obtained by the separation described above was dried in a static oven at 120° C. for 10 h. The dried material was then subjected to calcination at 500° C. in a static oven for 5 h.

b) Preparation of the Molding
Materials used:

| 60 g | the zeolite according to a) |
|---|---|
| 26.47 g | (15% SiO$_2$ on zeolite) Ludox ® AS-40 |
| 3 g | Walocel ® Wolf Walsrode AG PUFAS Werk KG |
| 77 mL | DI water |

60 g of the zeolite according to a), 26.47 g of 15% SiO$_2$ on zeolite and 3 g of Walocel® were combined and mixed in a kneader for 10 min. 77 mL of DI water were then added to the mixture which was kneaded until combined. The total kneading time was 30 min. The obtained zeolite was then calcined in the muffle furnace by raising the temperature at the rate of 3 K/min to 120° C. for 7 h followed by raising the temperature at the rate of 2 K/min to 500° C. for 2 h. 54 g of the molding with bulk density of 320 g/L were obtained.

c) Water Treatment
Materials used:

| 30 g | molding according to b) |
|---|---|
| 600 mL | DI water |

The molding of b) was suspended in DI water and heated at 145° C. for 8 h. The suspension was filtered. The zeolite was then dried at 120° C. for 12 h and calcined by raising the temperature at the rate of 2 K/min to 450° for 2 h. 33.4 g of the molding with bulk density of 330 g/L were obtained.

2.7 Preparation of a Zeolitic Material ZSM-5 Having Framework Type MFI

A ZSM-5 catalyst commercially available was water treated after shaping to impart mechanical strength. The NH3-TPD analysis of this material showed Brönsted acidity related to NH3-desorption above 250° C. The reaction for the preparation 3-methyl-3-buten-1-ol carried out with this catalyst was seen to be totally unselective. Selectivity is defined in this context as the molar amount of 3-methyl-3-buten-1-ol relative to the molar amount of formaldehyde brought into contact with the condensation catalyst.

Examples: Preparation of 3-methyl-3-buten-1-ol

E1. Using the Zeolitic Material Sn-BEA According to Reference Example 2.1 as Catalytically Active Material 55 g of an aqueous solution of formaldehyde (FA) (49 weight-%) were dissolved in 445 g of tert-butanol. A formaldehyde solution (5.39 weight-%) was obtained. This solution was dosed to an isothermal tubular reactor at 32 g/h (0.05 mol FA/h). The isobutene flask was pressurized with helium (to liquefy the gas) and pumped into the reactor at 31.3 g/h (0.55 mol/h). The two streams were pressurized to 20 bar and tempered to 100° C. before entering the reactor. The tubular reactor had a length of 110 cm and contained 10.85 g of a Sn-BEA catalyst according to Reference Example 2.1. The reactor was operated at 100° C. and at a constant pressure of 20 bar. The residence time was of about 15.67 min. The reaction was run for 48 h, and 4 samples were analysed during this time. After the reaction, the yield for 3-methyl-3-buten-1-ol based on the formaldehyde conversion was calculated with weight calibrated Gas Chromatography according to Reference Example 1.1. The unreacted formaldehyde was photometrically quantified according to Reference Example 1.1. The yield (Y), the selectivity (S) and the conversion (C) obtained are shown in Table 1 below.

E2. Using the Zeolitic Material Zr-MFI According to Reference Example 2.2 as Catalytically Active Material The protocol of Example E1 was repeated using Zr-MFI zeolite as catalyst. The tubular reactor was filled with 10.08 g of the Zr-MFI zeolite. The residence time was of 15.5 min. The reaction was run for 100 h and 9 samples were analysed during this time. After the reaction, the yield for 3-methyl-3-buten-1-ol based on the formaldehyde conversion was calculated with weight calibrated Gas Chromatography according to Reference Example 1.1. The unreacted formaldehyde was photometrically quantified according to Reference Example 1.1. The yield (Y), the selectivity (S) and the conversion (C) obtained are shown in Table 2 below.

TABLE 2

| Catalyst | After 6 h | | | After 24 h | | | After 30 h | | | After 48 h | | |
|---|---|---|---|---|---|---|---|---|---|---|---|---|
| | Y% | S% | C% | Y% | S% | C% | Y% | S% | C% | Y% | S% | C% |
| ZrMFI | 43 | 43 | 100 | 46 | 49 | 95 | 47 | 51 | 93 | 44 | 48 | 91 |

| After 54 h | | | After 72 h | | | After 78 h | | | After 96 h | | | After 102 h | | |
|---|---|---|---|---|---|---|---|---|---|---|---|---|---|---|
| Y% | S% | C% | Y% | S% | C% | Y% | S% | C% | Y% | S% | C% | Y% | S% | C% |
| 44 | 49 | 89 | 41 | 47 | 88 | 42 | 49 | 87 | 40 | 47 | 86 | 42 | 51 | 83 |

E3. Using the Zeolitic Material SnTI-MFI According to Reference Example 2.3 as Catalytically Active Material The protocol of example E1 was repeated using Sn—Ti-MFI zeolite as catalyst. The tubular reactor was filled with 10.15 g of the Sn—Ti-MFI zeolite. The residence time was of 155 min. The reaction was run for 100 h and 9 samples were analysed during this time. After the reaction, the yield for 3-methyl-3-buten-1-ol based on formaldehyde conversion was calculated with weight calibrated Gas Chromatography according to Reference example 1.1. The unreacted formaldehyde was photometrically quantified according to Reference Example 1.1. The yield (Y), the selectivity (S) and the conversion (C) obtained are shown in Table 3 below.

TABLE 3

| Catalyst | After 6 h | | | After 24 h | | | After 30 h | | |
|---|---|---|---|---|---|---|---|---|---|
| | Y% | S% | C% | Y% | S% | C% | Y% | S% | C% |
| Sn—Ti-MFI | 38 | 38 | 100 | 45 | 45 | 100 | 49 | 49 | 100 |

| After 48 h | | | After 52 h | | |
|---|---|---|---|---|---|
| Y% | Y% | Y% | Y% | S% | C% |
| 47 | 47 | 47 | 40 | 40 | 100 |

TABLE 1

| Catalyst | After 6 h | | | After 24 h | | | After 30 h | | | After 48 h | | |
|---|---|---|---|---|---|---|---|---|---|---|---|---|
| | Y% | S% | C% | Y% | S% | C% | Y% | S% | C% | Y% | S% | C% |
| SnBea | 70 | 71 | 99 | 72 | 72 | 100 | 73 | 73 | 99 | 71 | 72 | 99 |

| After 54 h | | | After 72 h | | | After 78 h | | | After 96 h | | | After 102 h | | |
|---|---|---|---|---|---|---|---|---|---|---|---|---|---|---|
| Y% | S% | C% | Y% | S% | C% | Y% | S% | C% | Y% | S% | C% | Y% | S% | C% |
| 67 | 68 | 99 | 69 | 69 | 99 | 67 | 68 | 99 | 69 | 70 | 99 | 67 | 68 | 99 |

Comparative Examples: Preparation of 3-methyl-3-buten-1-ol

CE1. Using the Zeolitic Material Ga-MWW According to Reference Example 2.4 as Catalytically Active Material The protocol of Example E1 was repeated using Ga-MWW zeolite as catalyst. The tubular reactor was filled with 10.10 g of the Ga-MWW zeolite. The residence time was of 15.5 min. The reaction was run for 28 h and 3 samples were analysed during this time. After the reaction, the yield for 3-methyl-3-buten-1-ol based on formaldehyde conversion was calculated with weight calibrated gas chromatography according to Reference Example 1.1. The unreacted formaldehyde was photometrically quantified according to Reference Example 1.1. The yield (Y), the selectivity (S) and the conversion (C) obtained are shown in Table 4 below.

TABLE 4

| | After 6 h | | | After 24 h | | | After 28 h | | |
|---|---|---|---|---|---|---|---|---|---|
| Catalyst | Y% | S% | C% | Y% | S% | C% | Y% | S% | C% |
| Ga-MWW | 7 | 7 | 100 | 9 | 9 | 100 | 10 | 10 | 100 |

CE2. Using the Zeolitic Material Ga-MFI According to Reference Example 2.5 as Catalytically Active Material The protocol of Example E1 was repeated using Ga-MFI zeolite as catalyst. The tubular reactor was filled with 10.20 g of the Ga-MFI zeolite. The residence time was of 15.5 min. The reaction was run for 39 h and 5 samples were analysed during this time. After the reaction, the yield for 3-methyl-3-buten-1-ol based on formaldehyde conversion was calculated with weight calibrated Gas Chromatography according to Reference Example 1.1. The unreacted formaldehyde was photometrically quantified according to Reference Example 1.1. The yield (Y), the selectivity (S) and the conversion (C) obtained are reported in Table 5 below.

TABLE 5

| | After 6 h | | | After 24 h | | | After 30 h | | | After 33 h | | | After 39 h | | |
|---|---|---|---|---|---|---|---|---|---|---|---|---|---|---|---|
| Catalyst | Y% | S% | C% | Y% | S% | C% | Y% | S% | C% | Y% | S% | C% | Y% | S% | C% |
| Ga-MFI | 29 | 30 | 100 | 35 | 35 | 98 | 34 | 34 | 99 | 28 | 28 | 100 | 34 | 34 | 99 |

CE3. Using the Zeolitic Material Fe-MFI/MEL According to Reference Example 2.6 as Catalytically Active Material The protocol of Example E1 was repeated using FeMFI/MEL zeolite as catalyst. This time the tubular reactor was filled with 10.10 g of the Fe MFI/MEL zeolite. The residence time was of 15.7 min. The reaction was run for 30 h and 3 samples were analysed during this time. After the reaction, the yield for 3-methyl-3-buten-1-ol based on formaldehyde conversion was calculated with weight calibrated Gas Chromatography according to Reference Example 1.1. The unreacted formaldehyde was photometrically quantified according to Reference Example 1.1. The yield (Y), the selectivity (S) and the conversion (C) obtained are reported in Table 6 below.

TABLE 6

| | After 6 h | | | After 24 h | | | After 28 h | | |
|---|---|---|---|---|---|---|---|---|---|
| Catalyst | Y% | S% | C% | Y% | S% | C% | Y% | S% | C% |
| FeMFI/MEL | 25 | 25 | 100 | 15 | 15 | 100 | 10 | 10 | 100 |

Results

As can be taken from the results above, the zeolitic materials of inventive examples E1 to E3 show a higher yield compared to all the zeolitic material of comparative examples CE1 to CE3 at a temperature of 100° C. In addition, the zeolitic materials of inventive examples E1 to E3 exhibit a higher selectivity at a temperature of 100° C. compared to the zeolitic material of comparative examples CE1 to CE3.

CITED LITERATURE

WO 2015/067654 A
WO 2014/060261 A
WO 2014/060259 A
Komatsu et al., Porous Material in Environmentally Friendly Processes, vol. 125, 1999, pages 507-514
US 2012059177 A
WO 2011/154330 A
WO 2011/147919 A
US 2011054083 A
Zhaoyang et al., Journal of Industrial and Engineering Chemistry, vol. 20, 2014, pages 4146-4151
Fernandes et al., Tetrahedron Letters, vol. 44, 2003, pages 1275-1278

The invention claimed is:
1. A process for preparing a compound of formula (II)

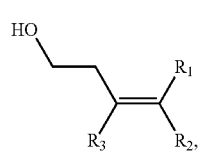

(II)

comprising
(i) providing a mixture comprising formaldehyde and a compound of formula (I)

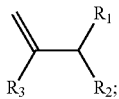 (I)

(ii) contacting the mixture, provided in (i) with a condensation catalyst comprising a zeolitic material, obtaining a mixture (ii) comprising the compound of formula (II);

wherein $R_1$, $R_2$ and $R_3$ are independently of each other selected from the group consisting of H, optionally substituted $C_1$-$C_{10}$ alkyl, optionally substituted $C_2$-$C_{10}$ alkenyl and optionally substituted aryl having from 6 to 12 carbon atoms;

wherein the framework structure of the zeolitic material in (ii) comprises Si, O, optionally Al, and a tetravalent element Y other than Si, which is one or more of Sn, Ti, Zr, and Ge, wherein in the framework structure of the zeolitic material in (ii), the molar ratio Al:Si is in the range of from 0:1 to 0.001:1, and wherein the framework structure of the zeolitic material in (ii) has framework type BEA, MFI, MWW, or a mixed structure thereof.

2. The process of claim 1, wherein Y is one or more of Sn and Zr.

3. The process of claim 1, where the framework structure of the zeolitic material in (ii) comprises Y in an amount of from 1 to 20 weight-%, based on the total weight of the zeolitic material.

4. The process of claim 1, wherein the framework structure of the zeolitic material in (ii) does not comprise a trivalent element X other than optionally Al.

5. The process of claim 1, wherein at least 99 weight-% of the framework structure of the zeolitic material in (ii) consist of Si, Y, O and H.

6. The process of claim 1, wherein the framework structure of the zeolitic material in (ii) has framework type BEA.

7. The process of claim 6, wherein the zeolitic material comprises Sn in an amount in the range of from 2 to 20 weight-% based on the total weight of the zeolitic material.

8. The process of claim 1, wherein the formaldehyde in (i) is one or more of aqueous formaldehyde, trioxane and paraformaldehyde.

9. The process of claim 1, wherein in the mixture provided in (i), the molar ratio of the compound of formula (I) relative to the formaldehyde, calculated as $CH_2O$, is in the range from 1:1 to 12:1.

10. The process of claim 1, wherein the mixture in provided in (i) additionally comprises a solvent.

11. The process of claim 1, wherein the contacting in (ii) is effected at a temperature of the mixture in the range of front 60 to 150° C.

12. The process of claim 1, wherein the contacting in (ii) is carried out in the liquid phase.

13. The process of claim 1, wherein $R_1$ and $R_2$ are each H and $R_3$ is $C_1$-$C_{10}$ alkyl.

14. The process of claim 1, wherein Y is one or more of Sn, Ti, Zr, and Ge.

15. The process of claim 1, wherein Y is Sn.

16. The process of claim 1, where the framework structure of the zeolitic material in (ii) comprises Y in an amount of from 4 to 16 weight-%, based on the total weight of the zeolitic material.

17. The process of claim 1, wherein at least 99.99 weight-% of the framework structure of the zeolitic material in (ii) consist of Si, Y, O and H.

* * * * *